US012539233B2

(12) United States Patent
Bader et al.

(10) Patent No.: US 12,539,233 B2
(45) Date of Patent: Feb. 3, 2026

(54) SYSTEMS, DEVICES, AND METHODS FOR REPLACING AN EYEDROPPER TIP ON AN EYEDROPPER BOTTLE WITH A REPLACEMENT EYEDROPPER TIP

(71) Applicant: OBBJECTIVES, LLC, St. Louis, MO (US)

(72) Inventors: Terry Bader, St. Louis, MO (US); Gregg J. Berdy, St. Louis, MO (US); Lanny Odin, Springfield, IL (US)

(73) Assignee: OBBJECTIVES, LLC, St Louis, MO (US)

( * ) Notice: Subject to any disclaimer, the term of this patent is extended or adjusted under 35 U.S.C. 154(b) by 87 days.

(21) Appl. No.: 18/140,432

(22) Filed: Apr. 27, 2023

(65) Prior Publication Data

US 2023/0301828 A1 Sep. 28, 2023

Related U.S. Application Data

(63) Continuation of application No. 17/118,245, filed on Dec. 10, 2020, now Pat. No. 11,679,026.

(60) Provisional application No. 62/946,258, filed on Dec. 10, 2019.

(51) Int. Cl.
*A61F 9/00* (2006.01)
*A61M 3/02* (2006.01)

(52) U.S. Cl.
CPC ......... *A61F 9/0008* (2013.01); *A61M 3/0279* (2013.01); *A61M 2207/10* (2013.01)

(58) Field of Classification Search
CPC ............... A61F 9/0008; A61M 3/0279; A61M 2207/10; A61M 3/0262; B67B 7/18; A61J 1/1412; A61J 1/1418
See application file for complete search history.

(56) References Cited

U.S. PATENT DOCUMENTS

| | | | | |
|---|---|---|---|---|
| 5,037,406 | A * | 8/1991 | Smith | A61F 9/0008 604/301 |
| 6,263,761 | B1 * | 7/2001 | Ryder | B67B 7/04 7/151 |
| 6,991,121 | B1 | 1/2006 | Kipperman et al. | |
| 10,640,276 | B2 | 5/2020 | McGrath et al. | |
| 10,695,216 | B2 | 6/2020 | Song et al. | |
| 10,723,526 | B1 * | 7/2020 | Aboabdo | B65D 43/0231 |
| 10,932,947 | B2 | 3/2021 | Enemark | |
| 11,203,467 | B2 | 12/2021 | Song et al. | |

(Continued)

FOREIGN PATENT DOCUMENTS

| | | | | |
|---|---|---|---|---|
| WO | WO-9503246 A1 * | 2/1995 | | A47K 5/1202 |
| WO | 9519931 A1 | 7/1995 | | |
| WO | WO-2007118124 A2 * | 10/2007 | | A61F 9/0008 |

*Primary Examiner* — Philip R Wiest
*Assistant Examiner* — Eric Rassavong
(74) *Attorney, Agent, or Firm* — Lewis Rice LLC

(57) ABSTRACT

Systems, devices, and methods for replacing an eyedropper tip on an eyedropper bottle with a replacement eyedropper tip. Such a system may include, without limitation, a removal tool, an application tool, and a replacement eyedropper tip. The removal tool may be used to remove a preexisting eyedropper tip on an eyedropper bottle, and the application tool may be used to apply the replacement eyedropper tip to the eyedropper bottle. In some embodiments, the replacement eyedropper tip and the application tool may be formed as a single unit or effectively be the same component.

14 Claims, 9 Drawing Sheets

(56) References Cited

U.S. PATENT DOCUMENTS

| | | | |
|---|---|---|---|
| 2004/0074925 | A1 | 4/2004 | Faurie |
| 2004/0182814 | A1 | 9/2004 | Suffa |
| 2004/0210203 | A1 | 10/2004 | Kusu et al. |
| 2005/0131358 | A1 | 6/2005 | Skolik |
| 2005/0274744 | A1 | 12/2005 | Spada et al. |
| 2006/0116649 | A1 | 6/2006 | Hagele |
| 2007/0233020 | A1 | 10/2007 | Hearne |
| 2009/0272769 | A1 | 11/2009 | Contreras et al. |
| 2010/0025354 | A1 | 2/2010 | Hansen |
| 2010/0224657 | A1 | 9/2010 | Bowman |
| 2013/0096517 | A1 | 4/2013 | Leistner et al. |
| 2013/0134186 | A1 | 5/2013 | Defemme et al. |
| 2014/0350492 | A1 | 11/2014 | Rojas Escalante et al. |
| 2019/0224044 | A1 | 7/2019 | Song et al. |
| 2019/0307641 | A1 | 10/2019 | Golub et al. |
| 2020/0276048 | A1 | 9/2020 | Hossain et al. |

* cited by examiner

SYSTEMS, DEVICES, AND METHODS FOR REPLACING AN EYEDROPPER TIP ON AN EYEDROPPER BOTTLE WITH A REPLACEMENT EYEDROPPER TIP

CROSS REFERENCE TO RELATED APPLICATIONS

This application is a Continuation of U.S. patent application Ser. No. 17/118,245 filed Dec. 10, 2020, which claims benefit of U.S. Provisional Patent Application No. 62/946,258 filed Dec. 10, 2019. The entire disclosure of all the above documents is herein incorporated by reference.

BACKGROUND OF THE INVENTION

Field of the Invention

This disclosure is related to the field of dropper bottles. More particularly to systems, devices, and methods for replacing an eyedropper tip on an eyedropper bottle with an alternative eyedropper tip.

Description of the Related Art

Ophthalmic solutions have been used to provide sterile, foreign-particle free eye drops to users' eyes for many, many years. Such solutions may have a number of uses, including without limitation delivering various substances to the eyes. For example, some ophthalmic solutions are used to transport eye-moisturizing molecules to a user's eyes. Ophthalmic solutions are generally sterilized to prevent contamination of the user's eyes with bacteria when the ophthalmic solution is dispensed into a user's eye. Similarly, ophthalmic solutions are generally foreign-particle free to prevent contamination of the user's eyes with foreign matter when the ophthalmic solution is dispensed into a user's eye. Both bacteria and foreign particles may injure a user's eye after being introduced, and accordingly, prior art devices have taken precautions against their inclusion in ophthalmic solutions.

Typically, ophthalmic solutions have been packaged for users as shown in FIG. 1 using eyedropper bottles (101) having eyedropper tips (102). Each eyedropper tip (102) will typically include a nose portion (133). Typically, the eyedropper bottles (101) have a known bottle shape, as depicted in FIG. 1. The elongated upper region (103) of the eyedropper bottle (101) will typically terminate in a round opening (105). Around the exterior portion of the upper region (103), there typically is a set of threads (107), which threads (107) may be used to secure a cap (109). The interior portion of the upper region (103) is typically smooth, although it may be threaded or include other features. This smooth region allows for the eyedropper tip (102) to be press-fit into the upper region (103). Said another way, the external diameter of the lower region (111) of the eyedropper tip (102) is slightly larger than the internal diameter of the upper region (103) of the eyedropper bottle (101). Thus, when the lower region (111) of the eyedropper tip (102) is pressed into the upper region (103) of the eyedropper bottle (101), the eyedropper tip (102) will remain attached to the eyedropper bottle (101) via an interference or friction fit. Although the embodiment depicted in FIG. 1 shows the eyedropper tip (102) designed to be attached to the eyedropper bottle (101) via an interference fit, any connection known in the art may be used. For example, in some embodiments, the eyedropper tip (102) may be attached to the eyedropper bottle (101) via a threaded connection.

One issue with typical eyedropper tips (102) is that they are generally static in their construction and operation. For example, a given eyedropper tip (102) is typically only able to produce drops of a certain size/volume, shape, and rate of flow, although the amount of pressure applied to the eyedropper bottle (101) may affect the rate of flow. Further, a given eyedropper tip (102) is typically only able to perform a set dropping method and operate in a set fashion. All of these characteristics flow from the design of the given eyedropper tip (102). However, unfortunately, it is difficult or impossible to change any characteristics of the drops produced by an eyedropper tip (102) design. Thus, the given eyedropper tip (102) may not be suitable for every use or every person's preference. This may result in a user of the eyedropper bottle (101) having the given eyedropper tip (102) desiring and/or needing to replace the eyedropper tip (102) on the eyedropper bottle (101), assuming that obtaining a new eyedropper bottle (101) having the same contents and a different, acceptable eyedropper tip (102) is not desired and/or feasible.

However, there is no current method or device to be used to replace eyedropper tips (102) on eyedropper bottles (101). As a result, problems may be encountered when attempting to change or replace eyedropper tips (102) used with eyedropper bottles (101). For example, it may be difficult to replace an eyedropper tip (102) because the eyedropper bottle (101), the related ophthalmic solution, and any replacement eyedropper tip must remain sterile and foreign-particle free during and after any eyedropper tip replacement.

This means that a user, or any other person, cannot touch the eyedropper tip or, often more importantly, a replacement eyedropper tip with any non-sterile device or appendage during and after any eyedropper tip replacement process. For example, an eyedropper tip (102) may likely be removed from an eyedropper bottle (101) by using a set of pliers or a user's hand. This process may be acceptable, as long as the process does not introduce any non-sterile elements into or onto the eyedropper bottle (101) during removal which can be difficult. Stated another way, non-sterile material may contact the removed eyedropper tip (102) because that tip will be thrown away, but the process may spread non-sterile elements unintentionally into the eyedropper bottle (101) or to areas around the opening (105) of the eyedropper bottle (101). This may be difficult, but is likely possible. It may be more difficult, however, to place a new eyedropper tip onto the eyedropper bottle (101) without contaminating the ophthalmic solution in the eyedropper bottle (101) or the replacement eyedropper tip (102). To prevent contamination, only a sterile device may touch a replacement eyedropper tip at any time. Thus, it may be very difficult to replace any given eyedropper tip on an eyedropper bottle filled with an ophthalmic solution.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, there is generally described herein systems, devices, and methods for replacing an eyedropper tip on an eyedropper bottle with a replacement eyedropper tip. Such a system may include, without limitation, a removal tool, an application tool, and a replacement eyedropper tip. The removal tool may be used to remove a preexisting eyedropper tip on an eyedropper bottle, and the application tool may be used to apply the replacement eyedropper tip to the eyedropper bottle. In some embodiments, the replacement eyedropper tip and the application tool may be formed as a single unit or effectively be the same component.

There is described herein, among other things, a system for replacing an existing eyedropper tip with a replacement eyedropper tip, the system comprising: a replacement eyedropper tip; a removal tool comprising; a main body having a bottom region including a first bottom hollowed out space and a top region having a first top hollowed out space; and grabber threads positioned in said first top hollowed out space, said grabber threads being sized and shaped to screwably engage an outer surface of a nose of an existing eyedropper tip; and an application tool comprising; a main body having a bottom region including a second bottom hollowed out space and a top region having a second top hollowed our space; and internal threads positioned in said second bottom hollowed out space, said internal threads being sized and shaped to engage with mating threads on an upper region of an eyedropper bottle; wherein said replacement eyedropper tip is positioned within said second bottom hollowed out space and said second top hollowed out space.

In an embodiment, the system further comprises a film across said bottom region of said application tool, said film enclosing said replacement eyedropper tip within said second bottom hollowed out space and said second top hollowed out space.

In an embodiment of the system, the application tool and said removal tool comprise separate components.

In an embodiment of the system, the application tool and said removal tool are connected together to form a single structure.

In an embodiment of the system, the grabber threads have a threading diameter which decreases when viewed from said bottom region to said top region.

In an embodiment of the system, the replacement eyedropper tip further includes: a top region comprising a nose; and a lower region having a smooth outer surface for engaging an inner surface of said upper region of said eyedropper bottle via an interference fit.

In an embodiment of the system, the smooth outer surface engages said inner surface of said upper region of said eyedropper bottle in said interference fit when said internal threads engage said mating threads.

In an embodiment of the system, the replacement eyedropper tip produces a drop from said eyedropper bottle having a different size from said drop produced by said existing eyedropper tip from said eyedropper bottle.

In an embodiment of the system, the replacement eyedropper tip produces a drop from said eyedropper bottle having a different shape from said drop produced by said existing eyedropper tip from said eyedropper bottle.

There is also described herein, a system for replacing an existing eyedropper tip with a replacement eyedropper tip, the system comprising: a removal tool comprising; a main body having a bottom region including a first bottom hollowed out space and a top region having a first top hollowed out space; and grabber threads positioned in said first top hollowed out space, said grabber threads being sized and shaped to screwably engage an outer surface of a nose of an existing eyedropper tip; and an application tool and replacement tip combination comprising; a main body having a bottom region including a second bottom hollowed out space and a top region having a second top hollowed our space, said bottom region and said top region being repeatedly separable from each other; internal threads positioned in said second bottom hollowed out space, said internal threads being sized and shaped to engage with mating threads on an eyedropper bottle; and a replacement eyedropper nose attached to said bottom region and positioned within said second top hollowed out space.

In an embodiment, the system further comprises a film across said bottom region of said application tool, said film enclosing said replacement eyedropper tip within said second bottom hollowed out space and said second top hollowed out space.

In an embodiment of the system, the grabber threads have a threading diameter which decreases when viewing from said bottom region to said top region of said removal tool.

In an embodiment of the system, the replacement eyedropper tip produces a drop from said eyedropper bottle having a different size from a drop produced by said existing eyedropper tip from said eyedropper bottle.

In an embodiment of the system, the replacement eyedropper tip produces a drop from said eyedropper bottle having a different shape from a drop produced by said existing eyedropper tip from said eyedropper bottle.

There is also described herein, a method for replacing an existing eyedropper tip with a replacement eyedropper tip, the method comprising: providing an eyedropper bottle having an existing eyedropper tip, said existing eyedropper tip including: a top region comprising a nose; and a lower region having a smooth outer surface engaging an inner surface of an upper region of said eyedropper bottle via an interference fit; providing a removal tool comprising; a main body having a bottom region including a first bottom hollowed out space and a top region having a first top hollowed out space; and grabber threads positioned in said first top hollowed out space; providing an application tool and replacement tip combination comprising; a main body having a bottom region including a second bottom hollowed out space and a top region having a second top hollowed our space, said bottom region and said top region being repeatedly separable from each other; internal threads positioned in said second bottom hollowed out space; and a replacement eyedropper nose attached to said bottom region and positioned within said second top hollowed out space; screwing said replacement tool onto said nose of said existing eyedropper tip so said grabber threads engage an outer surface of said nose of said existing eyedropper tip; pulling on said replacement tool to break said interference fit and separate said eyedropper tip from said eyedropper bottle; screwing said internal threads onto mating threads positioned on an external surface of said upper region of said eyedropper bottle; removing said top region of said application tool from said bottom portion of said application tool; and dispensing material from said eyedropper bottle through said replacement eyedropper nose.

In an embodiment, the method further comprises: removing a film enclosing said replacement eyedropper tip within said second bottom hollowed out space and said second top hollowed out space from across said bottom region of said application tool prior to screwing said internal threads onto said mating threads.

In an embodiment of the method, the grabber threads have a threading diameter which decreases when viewing from said bottom region to said top region of said removal tool.

In an embodiment of the method, the replacement eyedropper nose produces a drop during said dispensing having a different size from a drop produced by said existing eyedropper tip.

In embodiments of the method, the replacement eyedropper nose produces drops having a volume of less than 45 microliters, less than 30 microliters, less than 20 microliters, or about 22 microliters.

In an embodiment of the method, the replacement eyedropper nose produces a drop during said dispensing having a different shape from a drop produced by said existing eyedropper tip.

DETAILED DESCRIPTION OF PREFERRED EMBODIMENTS

This disclosure relates to systems, devices, and methods for replacing an eyedropper tip on an eyedropper bottle with a replacement eyedropper tip. Specifically, the system for replacing an eyedropper tip on an eyedropper bottle may include (a) a removal tool such as that shown in FIGS. 14-20, (b) an application tool such as that shown in FIGS. 8-13, and (c) a replacement eyedropper tip such as that shown in FIGS. 2-7. These components may be integrated together in some embodiments such as it shown in FIGS. 22 and 23 which combine a replacement eyedropper tip with the application tool which also functions as a cap for the resultant bottle. Alternatively, the various devices may be provided independently of each other or a subset of devices may be provided without others.

Figure 1:
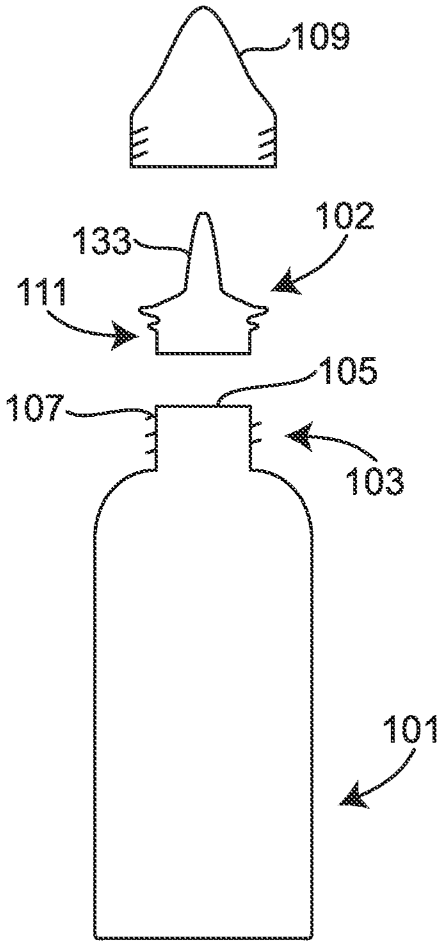
FIG. 1 depicts a cross-sectional view of a typical eyedropper bottle with eyedropper tip and cap.
Figure 2:
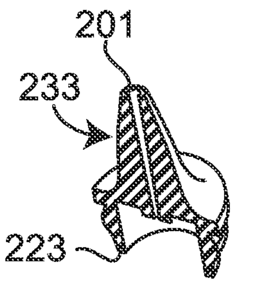
FIGS. 2, 3, 4, 5, 6, and 7 depict various views of an embodiment of a replacement eyedropper tip.
Figure 3:
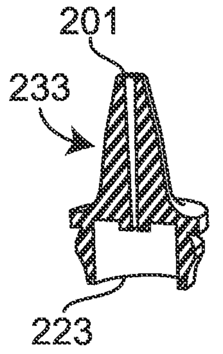
Figure 4:
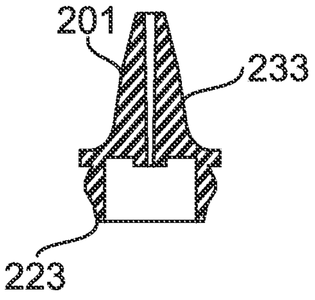
Figure 8:
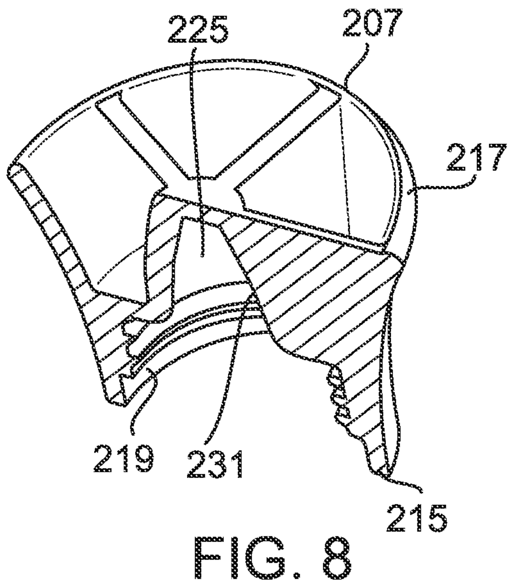
FIGS. 8, 9, 10, 11, 12, and 13 depict various views of an embodiment of an eyedropper tip application tool.
Figure 14:
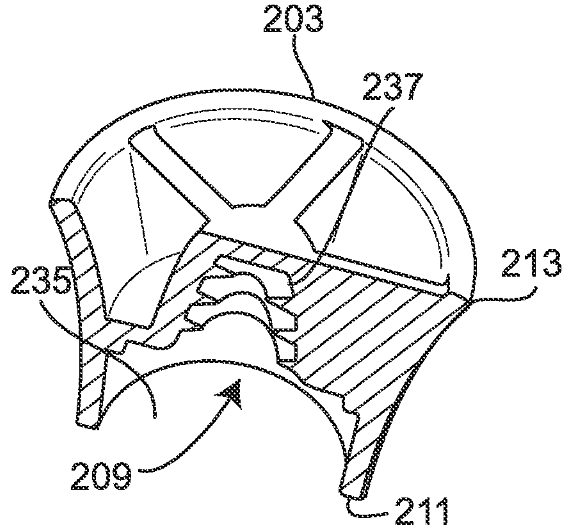
FIGS. 14, 15, 16, 17, 18, 19, and 20 depict various views of an embodiment of an eyedropper tip removal tool.

FIGS. 2, 8, and 14 depict a cross-sectional, perspective view of an embodiment of a system for replacing an eyedropper tip (102) on an eyedropper bottle (101) as shown in FIG. 1 with a replacement eyedropper tip (201). The eyedropper tip replacement system can include, without limitation, (a) the replacement eyedropper tip (201, FIG. 2); (b) an application tool (207, FIG. 8); and (c) a removal tool (203, FIG. 14).

The replacement eyedropper tip (201), depicted in FIG. 2, will generally be similar to many known eyedropper tips, however, the replacement eyedropper tip (201) will generally be capable of producing eye drops that have characteristics preferred or desired by the user of the eyedropper bottle, which characteristics will typically be different from those of the original eyedropper tip. Without limitation, the replacement dropper tip (201) may produce drops having a different volume, shape, or other characteristic compared to drops produced by the old eyedropper tip (102)

The replacement eyedropper tip (201) will typically include at least a bottom region (223) and a nose portion (233). The nose portion (233) is typically shaped as a generally conical frustum, which frustum may have generally convex or concave sides. In other embodiments, the nose portion (233) may be shaped as a generally pseudospherical surface of hyperbolic or parabolic type. The replacement eyedropper tip (201) may be formed from any material. Typically, the replacement eyedropper tip (201) may be formed of a thermoplastic or other material that may be used during mass production. Further, the material used to make the replacement eyedropper tip (201) will typically be able to withstand sterilization (or other cleaning process) and will not react with any ophthalmic solution stored in the eyedropper bottle (101). As used herein, the term "sterile" and its various forms will be used to mean sufficiently free from bacteria and other contaminants such that use of the sterile thing will not likely cause problems or infections for a user. In other words, "sterile" as used herein will mean "substantially clean" and may not rise to the level of completely sterile as that term may be used scientifically.

The replacement eyedropper tip (201), in some embodiments, may be formed into any shape or size as long as the lower region (111) of the eyedropper lid (201) will fit into the round opening (105) of the eyedropper bottle (101). Further, in an embodiment, the shape and size of the replacement eyedropper tip (201) will generally produce drops, when used with the eyedropper bottle (101), of a size that will produce less than typical waste when applied to a user's eyes. Such waste, in this context, may be spillage that leaks over the lower eyelid or into the tear ducts. In some embodiments, the replacement eyedropper tip (201) may produce drops having a volume of less than 45 microliters. In other embodiments, the replacement eyedropper tip (201) may produce drops having a volume of less than 30 microliters. In yet other embodiments, the replacement eyedropper tip (201) may produce drops having a volume of less than 20 microliters. In yet other embodiments, the replacement eyedropper tip (201) may produce drops having a volume of about 22 microliters.

The application tool (207) depicted in FIG. 8 will generally be capable of applying the replacement eyedropper tip (201) to an eyedropper bottle (101) after the preexisting eyedropper tip (102) is removed. The main body of the application tool (207) may be formed from any material. Typically, the application tool (207) may be formed of a thermoplastic or other material that may be used during mass production. Further, the material used to make the application tool (207) will typically be able to withstand the stresses of (a) applying a replacement eyedropper tip (201) to an eyedropper bottle (101) and (b) sterilization. The application tool (207) may be formed into any shape or size that will facilitate applying a replacement eyedropper tip (201) to an eyedropper bottle (101). Generally, the application tool (207) will be of a sufficient size and shape to fit over the replacement eyedropper tip (201) and the eyedropper bottle (101).

In some embodiments, the application tool (207) will be sized so that the application tool (207) may be threaded onto the threads (107) of the eyedropper bottle (101). In the embodiment depicted in FIG. 8, the application tool (207) has a generally columnar shape with some flaring from a bottom region (215) of the application tool (207) to a top end of the top region (217) of the application tool (207). The flaring may provide a surface for a user to effectively grip the application tool (207). The bottom region (215) and top region (217) essentially divide the application tool (207) into generally equal halves. Other views of the embodiment of the application tool (207) depicted in FIG. 8 may be seen in FIGS. 9-13.

In the embodiment depicted in FIG. 8, the application tool (207) may include a first hollowed out space (225) that is shaped and sized to accommodate at least a portion of a replacement eyedropper tip (201). In some embodiments, the first hollowed out space (225) may be formed to have some internal threads (219) that may extend from a position proximate to the bottom end of the bottom region (215) to the top region (217). The region of the first hollowed out space (225) proximate to the internal threads (219) may have a generally cylindrical shape. The internal threads (219) typically begin in the bottom region (215) of the application tool (207) and at or near the top region (217) of the application tool (207). The internal threads (219) may have a consistent diameter or may have a varied diameter. In an embodiment, the thread diameter will be set so that the internal threads (219) will have a diameter that will mate with the threads (107) on the eyedropper bottle (101). For these embodiments, the application tool (207) may be threaded onto the eyedropper bottle (101).

Further, in the depicted embodiment, above the internal threads (219) may be a first tip-receiving region (231) that extends from the bottom region (215) to a position proximate to the top end of the top region (217). The first tip-receiving region (231) is typically shaped as a generally conical frustum, which frustum may have generally convex or concave sides. In other embodiments, the first tip-receiving region (231) may be shaped as a generally pseudospherical surface of hyperbolic or parabolic type. The first tip-receiving region (231) may typically have flat surfaces. The first tip-receiving region (231) may include a flat portion that is the portion of the first tip-receiving region (231) that is most proximate to the top end of the top region (217). This flat portion, in combination with the geometry of the remainder of the first tip-receiving region (231), may function to press a related replacement eyedropper tip (201) into the eyedropper bottle (101) being modified. Accordingly, the shape and design of the first tip-receiving region (231) may fit sufficiently close to the replacement eyedropper tip (201) to transfer pressure from the replacement tool (207) to the replacement eyedropper tip (201).

There may be a first transition region between the internal threads (219) and the first tip-receiving region (231). The first transition region may be any shape and size but will typically include a convex curve to allow the diameter of the first hollowed out space (225) to transition from a greater diameter at the internal threads (219) to a lesser diameter at the first tip-receiving portion (231). The greater diameter at the internal threads (219) will typically be the same diameter of the threads (107) on the related eyedropper bottle (101). The lesser diameter will typically be the same diameter as, or slightly less than, the diameter of the eyedropper tip (201) being placed onto the eyedropper bottle (101). This close or tight fit may allow the replacement eyedropper tip (201) to remain attached to the application tool (207) until the replacement eyedropper tip (201) has been installed into the eyedropper bottle (101).

Figure 9:
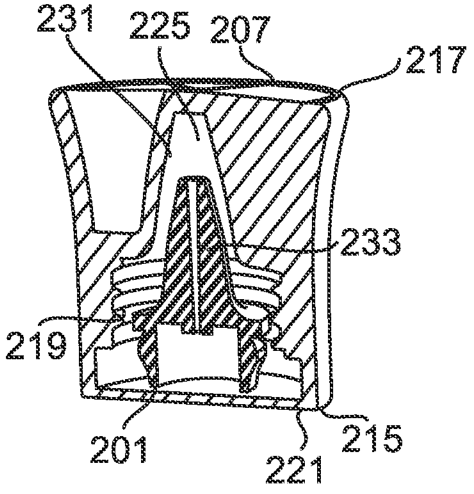

As best shown in FIG. 9, the application tool (207) may include a film (221) that covers at least a portion of the bottom region (215) of the application tool (207). This film (221) may be any film capable of preventing ingress of pathogens or foreign particles into the bottom region (215) of the application tool (207). This may also allow the application tool (207) to be sterilized and then remain sterile within the area enclosed by the film (221). The replacement eyedropper tip (201) may also be placed within the application tool (207) under the film (221), so that both the replacement eyedropper tip (201) and the application tool (207) may be sterilized together and/or remain in a sterilized condition together. When the film (221) is present, it may serve as a convenient, sterile packaging for both the replacement eyedropper tip (201) and the portion of the application tool (207) that should remain sterile.

The removal tool (203) depicted in FIGS. 14-20 will generally be capable of removing a preexisting eyedropper tip (102) from an eyedropper bottle (101). The main body of the removal tool (203) may be formed from any material. Typically, the removal tool (203) may be formed of a thermoplastic or other material that may be used during mass production. Further, the material used to make the removal tool (203) will typically be able to withstand the stresses of removing an eyedropper tip (102) from an eyedropper bottle (101). The removal tool (203) may be formed into any shape or size that will facilitate removal of an eyedropper tip (102). Generally, the removal tool (203) will be sufficiently shaped and sized to fit over a typical eyedropper tip (102).

In some embodiments, the removal tool (203) will be sized so that the removal tool (203) may be used to grip and retain the eyedropper tip (102) being removed and replaced. In the embodiment depicted in FIG. 14, the removal tool (203) has a generally columnar shape with some flaring from the bottom region (211) of the removal tool (207) to the top region (213) of the removal tool (203). The flaring may provide a surface for a user to effectively grip the removal tool (203). The bottom region (211) and top region (213) essentially divide the removal tool (203) into generally equal, contiguous halves. Other views of the embodiment of the removal tool (203) depicted in FIG. 14 may be seen in FIGS. 15-20.

In the embodiment depicted in FIGS. 14-20, the removal tool (203) may include a second hollowed out space (235) that is shaped and sized to accommodate at least a portion of an eyedropper tip (102). In some embodiments, the second hollowed out space (235) may be formed to have surfaces in the bottom region (211) that are smooth. The second hollowed out space (235) in the bottom region (211) will typically may have a generally cylindrical shape.

Further, in the depicted embodiment, above the smooth bottom region (211) may be a second tip-receiving region (237) that extends from the bottom region (211) to a position proximate to the top end of the top region (213). The second tip-receiving region (237) is typically shaped as a generally conical frustum, which frustum may have generally convex or concave sides. In other embodiments, the second tip-receiving region (237) may be shaped as a generally pseudospherical surface of hyperbolic or parabolic type. The second tip-receiving region (237) may include a flat portion that is the portion of the second tip-receiving region (237) that is most proximate to the top end of the top region (213). The other surfaces of the second tip-receiving region (237) may include some internal grabber threads (209).

The internal grabber threads (209) typically begin at or above a bottom region (211) of the removal tool (203) at a first thread diameter and end proximate to the top of the top region (213) of the removal tool (203) at a second thread diameter, wherein the second thread diameter is smaller than the first thread diameter. Said another way, the threading diameter typically decreases as the threads move from a position at or above the bottom region (211) towards the top of the top region (213). In an embodiment, the thread diameters will be set so that at least some of the internal grabber threads (209) will have a diameter that is less than the diameter of typical eyedropper tips (102), allowing the internal grabber threads (209) to “bite” into a given eyedropper tip (102). Further, this variable diameter of the internal grabber threads (209) may allow for the internal grabber threads (209) to bite into different sized and shaped eyedropper tips (102), at least at some point along the nose (133) of the eyedropper tip (102), as long as the given nose (133) is at least similar to a typical nose (133) in shape and size. The internal grabber threads (209) generally extend from the surfaces of the second hollowed out space (235) in a helix or helix-like form. For these embodiments, the length of the internal grabber threads (209) may be any length sufficient to allow the removal tool (203) to create an interference between the internal grabber threads (209) and an eyedropper tip (102) to be removed. After the internal grabber threads (209) “bite” into the eyedropper tip (102), the internal grabber threads (209) and the eyedropper tip (102) will be connected via the interference between the two. Accordingly, the user may then pull the eyedropper tip (102) off of the eyedropper bottle (101) using the removal tool (203) because the interference connection will pull the eyedropper tip (102) as the removal tool (203) is pulled.

There may be a second transition region between the bottom portion (211) and the second tip-receiving region (237). The second transition region may be any shape and size but will typically include a convex curve to allow the diameter of the second hollowed out space (235) to transition from a greater diameter at the bottom region (211) to a lesser diameter at the second tip-receiving portion (237). The greater diameter at the bottom region (211) will typically be the same diameter as the overall diameter of the region of the internal threads (219) of the application tool (207). The lesser diameter will typically be the same diameter as, or slightly greater than, the diameter of the eyedropper tip (201) being removed from the eyedropper bottle (101). This additional space may allow for the internal grabber threads (209) to be constructed to a sufficient height to be capable of biting into a related eyedropper tip (102) being removed.

In some embodiments, the internal grabber threads (209) of the removal tool (203) may be deeper (the height of the threads greater) than the internal threads (219) of the application tool (207). Further, in some embodiments, the internal grabber threads (209) of the removal tool (203) may be less rounded at their crests than the internal threads (219) of the application tool (207). In yet other embodiments, the internal grabber threads (209) may be replaced with anything capable of securing an eyedropper tip (102) to the removal tool (203), including without limitation a spike, an adhesive, a wedge, a set of arms, or other tool known in the art.

Typically, eyedropper tips (102) on eyedropper bottles (201) do not include threads on their exterior surfaces. However, in some specialty applications, or in future applications, it is contemplated that some eyedropper tips (102) may include threads on the exterior surfaces. In such an embodiment, the internal grabber threads (209) of the removal tool (203) may be designed to mate with the thread on the eyedropper tip (102) being removed. In these embodiments, the internal grabber threads (209) do not “bite” into the eyedropper tip (102), but instead, the internal grabber threads (209) mate with the threads on the eyedropper tip (102). This mating may allow a user to pull off or screw off the eyedropper tip (102).

The components of the system for replacing a preexisting eyedropper tip (102) on an eyedropper bottle (101) with a replacement eyedropper tip (201) may be made from the same material. For example, the replacement eyedropper tip (201), the removal tool (203), and the application tool (207) may all be made from the same material. In such an embodiment, each component of the system may be molded or otherwise made at the same time, or alternatively, may be molded or otherwise made at different times. In other embodiments, the components of the system may be made from different materials. In an embodiment, the removal tool (203) and the application tool (207) may be integrally formed.

Figure 10:
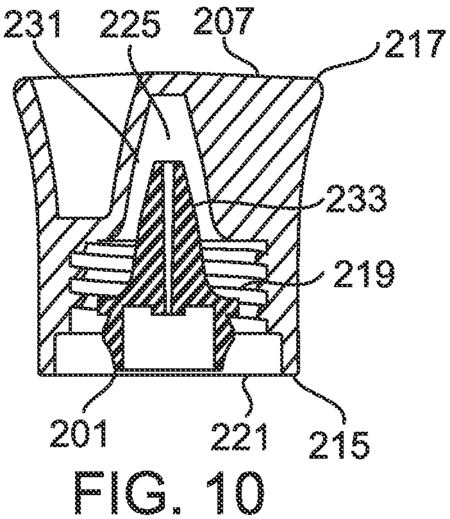
Figure 15:
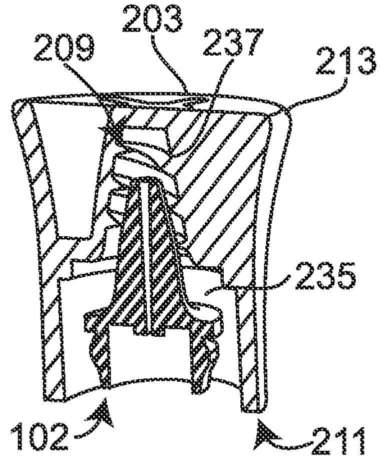
Figure 16:
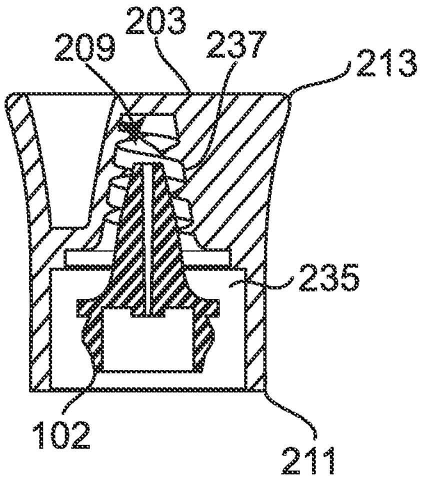
Figure 17:
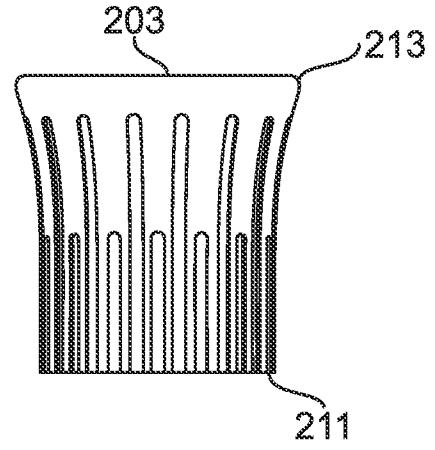
Figure 18:
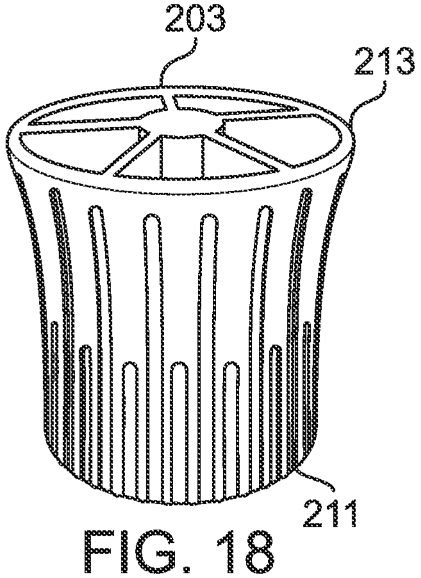

FIGS. 2-7 depict an embodiment of the replacement eyedropper tip (201) that may be applied to an eyedropper bottle (101) containing an ophthalmic solution. FIGS. 9 and 10 best depict an embodiment of the application tool (207) with the replacement eyedropper tip (201) inside. The film (221) encloses the replacement eyedropper tip (201) inside of the application tool (207). FIGS. 15 and 16 depict an embodiment of the eyedropper tip (102), but in this figure, the eyedropper tip (102) has internal grabber threads (209) of the removal tool (203) embedded, or “biting,” into it. This may allow a user to remove the eyedropper tip (102) from the eyedropper bottle (101). The removal may be accomplished by pulling the eyedropper tip (102) from an interference fit with the eyedropper bottle (101), by twisting the eyedropper tip (102) to unthread the eyedropper tip (102) from the eyedropper bottle (101), or by another action as would be known in the art. For example, after the internal grabber threads (209) of the removal tool (203) embedded in the eyedropper tip (102), the eyedropper tip (102) may be removed by pulling the removal tool (203) away from the eyedropper bottle (101) and gently rocking the removal tool (203), side to side or otherwise.

Figure 5:
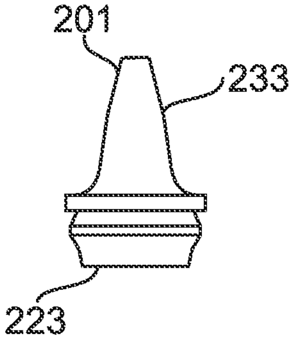
Figure 6:
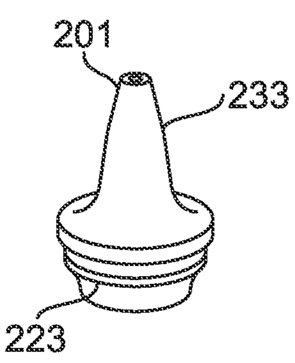
Figure 11:
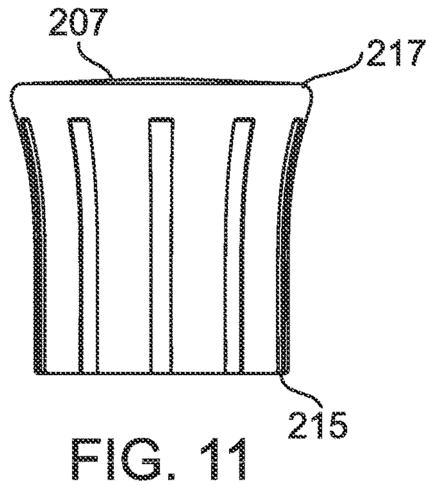
Figure 12:
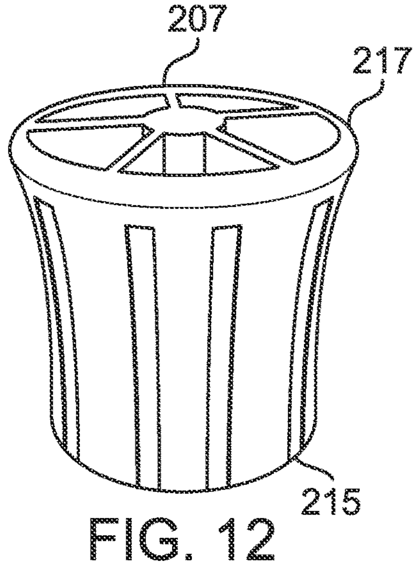

FIGS. 5 and 6 depict side and perspective views of the replacement eyedropper tip (201). FIGS. 11 and 12 depict side and perspective views of the application tool (207) having a top region (217) and a bottom region (215). In the embodiment depicted in FIGS. 11 and 12, the application tool (207) may have textured sides to provide grip for the user. For example, the embodiment of the application tool (207) depicted in FIGS. 11 and 12 includes scalloped sections that create a grippable texture. In other embodiments, the application tool (207) may have a different shape. In other embodiments, the application tool (207) may have a different texture or no texture. In the embodiment depicted in FIGS. 17 and 18, the removal tool (203) may have textured sides to provide grip for the user. For example, the embodiment of the removal tool (203) depicted in FIGS. 17 and 18 includes scalloped sections that create a grippable texture. In other embodiments, the removal tool (207) may have a different shape. In other embodiments, the removal tool (207) may have a different texture or no texture.

Figure 7:
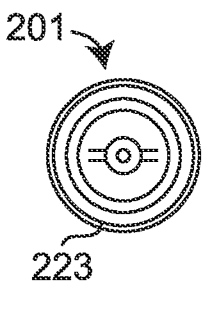
Figure 13:
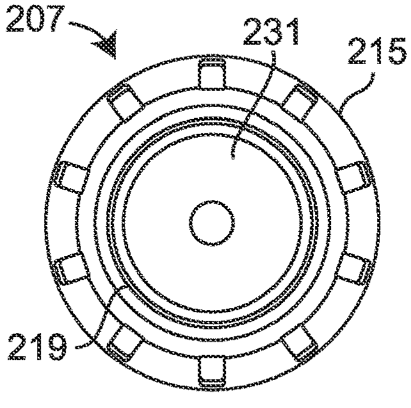
Figure 19:
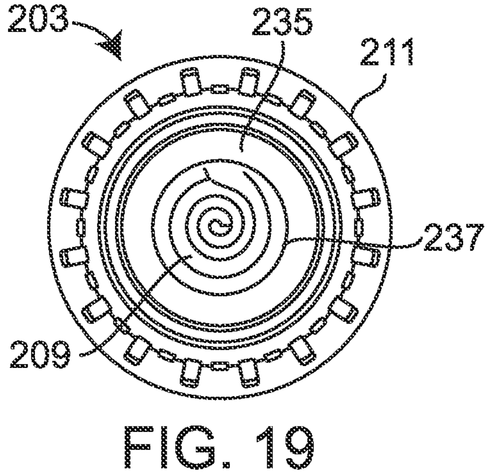
Figure 20:
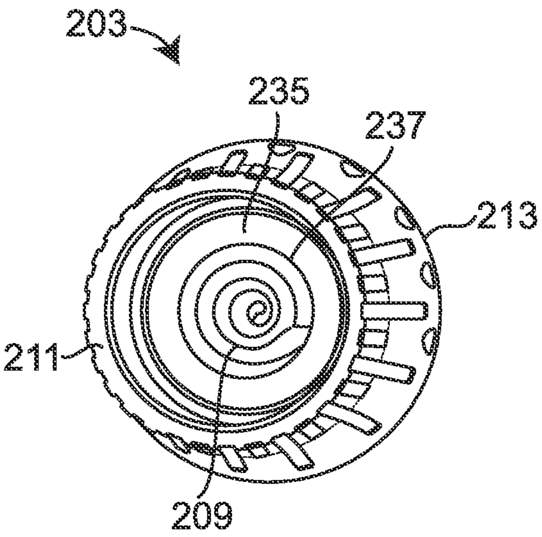

FIG. 7 depicts a bottom view of the replacement eyedropper tip (201), which view specifically shows the bottom region (223) of the replacement eyedropper tip (201). FIG. 13 depicts a bottom view of the application tool (207), which specifically shows the internal threads (219) and bottom region (215) of the application tool (207). FIG. 19 depicts a bottom view of the removal tool (203), which specifically shows the internal grabber threads (209) and bottom end (211) of the removal tool (203). FIG. 20 shows a bottom perspective view of the removal tool (203), which specifically shows the internal grabber threads (209) and bottom end (211) of the removal tool (203).

Figure 21:
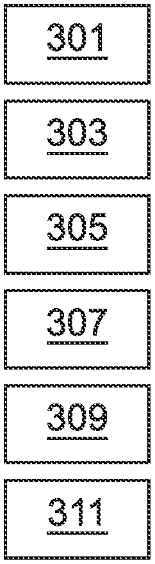
FIG. 21 depicts a block diagram of an embodiment of a method for replacing an eyedropper tip on an eyedropper bottle with a replacement eyedropper tip that uses the devices and systems described in this application.

FIG. 21 depicts a block diagram of an embodiment of a method for replacing a preexisting eyedropper tip (102) on an eyedropper bottle (101) with a replacement eyedropper tip (201) that uses the devices and systems described above. One step (301) to the depicted method is to provide an eyedropper bottle (101) having a preexisting eyedropper tip (102). Another step (303) to the depicted method is to provide a system for replacing a preexisting eyedropper tip (102) on an eyedropper bottle (101) with a replacement eyedropper tip (201). In some embodiments, the system comprises (a) a replacement eyedropper tip (201); (b) a removal tool (203); and (c) an application tool (207). In some embodiments, the replacement eyedropper tip (201) may be included in the application tool (207), contained within a film (221). In other embodiments, each of the components of the system may be separately provided. In some embodiments, each of the components of the system may be provided in a sterile manner, such as being provided in a sterile container or package.

Another step (305) to the depicted method is to thread the removal tool (203) on to the preexisting eyedropper tip (102) to be removed. For special or future eyedropper tips (102) that include threads, this step (305) may involve threading the removal tool (203) onto the threads of the eyedropper tip (102). For typical eyedropper tips (102) without threads, this step (305) may involve threading the internal grabber threads (209) of the removal tool (203) into the dropper portions of the eyedropper tip (102). In this case, the internal grabber threads (209) may be threaded (or "bite") into the eyedropper tip (102) until the eyedropper tip (102) is sufficiently connected to the removal tool to overcome the interference fit and stay attached to the removal tool (203) when being removed from the eyedropper bottle (101).

Another step (307) to the depicted method is to remove the eyedropper tip (102) using the attached removal tool (203). For eyedropper tips (102) having threads, the removal tool (203) may be rotated until the eyedropper tip (102) is unthreaded and separated from the eyedropper bottle (101). For eyedropper tips (102) not having threads, the removal tool (203) is pulled away from the eyedropper bottle (101) and gently rocked until the interference fit between the eyedropper tip (102) and the eyedropper bottle (101) is overcome and the eyedropper tip (102) is separated from the eyedropper bottle (101). In either case, once the eyedropper tip (102) is removed from the eyedropper bottle (101), both the eyedropper tip (102) and the removal tool (203) may be set aside or discarded.

Another step (309) to the depicted method is to prepare the replacement eyedropper tip (201) and the application tool (207) for placement of the replacement eyedropper tip (201) onto the eyedropper bottle (101). In embodiments where the replacement eyedropper tip (201) is included in a sterilized portion of the application tool (207), the film (221) that acts as a barrier from pathogens and foreign particles is removed. Further, if not already installed into the application tool (207), the replacement eyedropper tip (201) is installed into the application tool (207). In embodiments wherein the replacement eyedropper tip (201) and the application tool (207) are either separately packaged or packaged together, the packages are removed. Then the replacement eyedropper tip (201) is installed into the application tool (207). In any case, the replacement eyedropper tip (201) will be installed into the application tool (207) without the user touching the replacement eyedropper tip (201).

Another step (311) is to install the replacement eyedropper tip (201) into the eyedropper bottle (101) using the application tool (207). In embodiments where the eyedropper tips (102, 201) and eyedropper bottle (101) have threads, the replacement eyedropper tip (201) is placed into or onto the threads on the eyedropper bottle (101) using the application tool (207). The replacement eyedropper tip (201) is then threaded into the eyedropper bottle (101) threads until the connection between the replacement eyedropper tip (201) and the eyedropper bottle (101) is sufficiently tight to ensure that the replacement eyedropper tip (201) will remain with the eyedropper bottle (101) and that the connection will not leak. In embodiments where the eyedropper tips (102, 201) and eyedropper bottle (101) do not have threads, the replacement eyedropper tip (201) is placed into the round opening (105) of the eyedropper bottle (101) using the application tool (207). The replacement eyedropper tip (201) is then pressed into the eyedropper bottle (101) until the connection between the replacement eyedropper tip (201) and the eyedropper bottle (101) is sufficiently tight to ensure that the replacement eyedropper tip (201) will remain with the eyedropper bottle (101) and that the connection will not leak. This may also include threading the internal threads (219) of the application tool (207) onto the threads (107) of the eyedropper bottle (101), which in turn may press the components together. In either case, the eyedropper tip (201) will be forced into the round opening (105) of the replacement eyedropper bottle (101), creating an interference fit.

Note that generally steps (305) and (307) need not be as sterile as steps 309 and 311. This is may be due to the removed eyedropper tip (102) being discarded after step (307), whereas the replacement eyedropper tip (201) must remain sterile (or at least generally clean) because it will be used subsequently to dispense the ophthalmic solution from the eyedropper bottle (101). It may be that the principal concern for steps (305) and (307) is that pathogens and other foreign particles are not introduced into the ophthalmic solution or the regions of eyedropper bottle (101) where pathogens and foreign particles may be introduced into the ophthalmic solution. However, for steps (305) and (307), the replacement eyedropper tip (201) should remain sterile (or at least generally clean) in its entirety because it will be used going forward with the eyedropper bottle (101). Thus, no (or very few) pathogens or foreign particles may be introduced onto the surfaces of the nose portion (233) or other portions of the replacement eyedropper tip (201).

In some embodiments, the removal tool (203) and the application tool (207) may be formed as a single unit. For example, in some embodiments, the top region (213) of the removal tool (203) may be connected to the top region (217) of the application tool (207). In other embodiments where the removal tool (203) and the application tool (207) may be formed as a single, integrated unit, the bottom region (215) of the application tool (207) may be connected to the bottom region (211) of the removal tool (203). In yet other embodiments, either of the bottom region (215) or the top region (217) of the application tool (207) may be connected to either of the bottom region (211) or the top region (213) of the removal tool (203). In any such embodiment, the removal tool (203) and the application tool (207) may be formed together during manufacturing. Alternatively, the removal tool (203) and the application tool (207) may be formed separately during manufacturing but bonded together (or otherwise connected) subsequent to forming.

Figure 22:
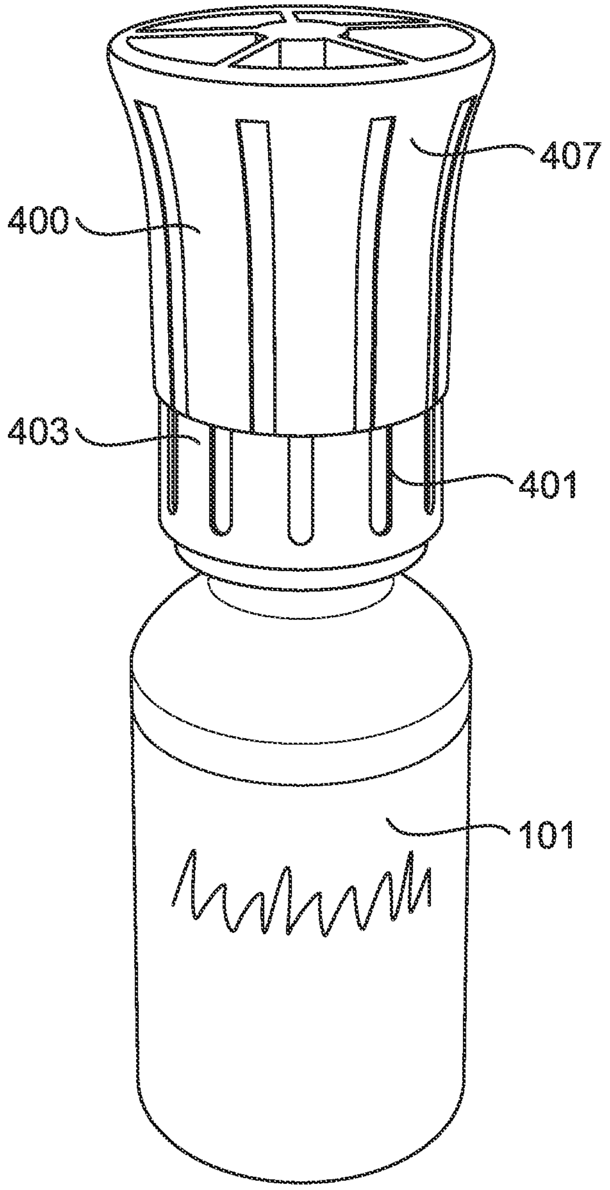
FIGS. 22 and 23 depict an embodiment of an application tool combined with a removal tool, along with a replacement eyedropper tip.
Figure 23:
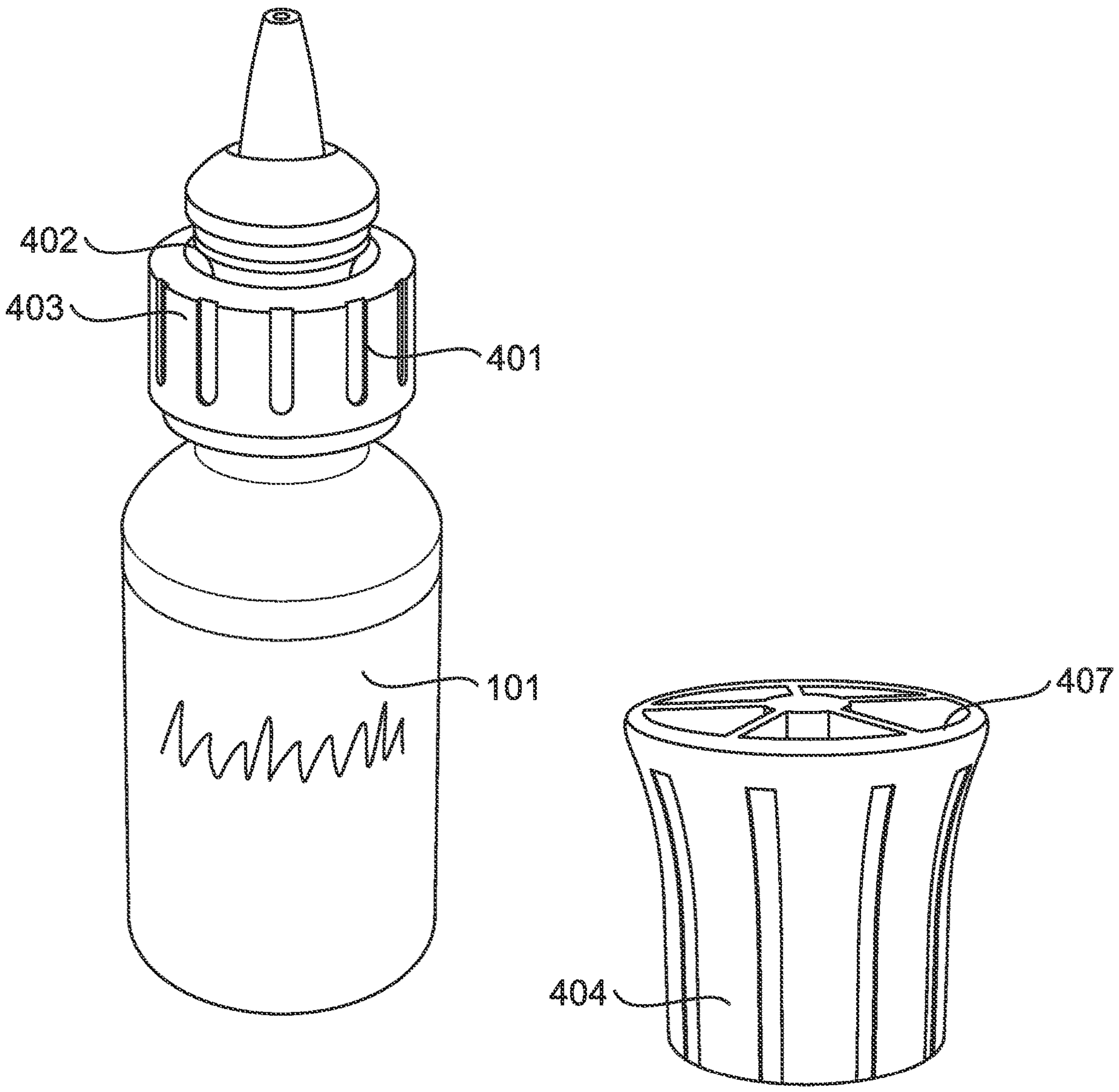

In another embodiment, as depicted in FIGS. 22 and 23, a replacement eyedropper tip (401) and an application tool (407) may be formed as a single unit (400), wherein the replacement eyedropper tip (401) and application tool (407) may be separated, and wherein the application tool (407) may serve as a protective cap after installation of the replacement eyedropper tip (401). In the depicted embodiment, the application tool (407) is shown to be a protective snap on/off cap. In this embodiment, the eyedropper tip (401) may be manually screwed onto the eyedropper bottle (101) without the use of the application tool (407), although the application tool (407) may alternatively be used for this function. So again, in this embodiment, the application tool (407) may primarily serves as a protective snap on/off cap for the replacement eyedropper tip (401). Additionally, the application tool (407) and the replacement eyedropper tip (401) may be integrally formed. For this embodiment, the replacement eyedropper tip (401) shares many of the features, uses, and constructions with the replacement eyedropper tip (201) of the first embodiment discussed above. Further, the application tool (407) shares many of the features, uses, and constructions with the application tool (207) of the first embodiment discussed above.

As shown in FIG. 22, the single unit (400) may be made of a replacement eyedropper tip (401) and an application tool (407) connected together as a single part. Specifically, as shown in FIG. 23, portions of the replacement eyedropper tip (401) integrated into a collar (403) of the replacement eyedropper tip (401) may snap into a bottom (404) of the application tool (407). As shown in FIG. 23, the replacement eyedropper tip (401) and the application tool (407) may be separated from each other. The connection between the replacement eyedropper tip (401) and the application tool (407) may be made by a friction fit between the bottom of the eyedropper portion of the replacement eyedropper tip (401) and the lower portions of the application tool (407). In other words, the exterior diameter of the replacement eyedropper tip (401) at or around the midpoint (402) of the replacement eyedropper tip (401) may be slightly larger than the interior diameter of the bottom (404) of the application tool (407). The bottom portion of the application tool may, in such an embodiment, be attached to a replacement eyedropper nose with the two pieces forming the replacement eyedropper tip (401) and the upper portion of the application tool forming a reusable cover to protect the replacement eyedropper nose. In such an embodiment, the application tool (407) effectively may form the replacement eyedropper tip (401) with the two components effectively being the same.

In such an embodiment, the single unit may be sterilized (or at least be generally clean), and the connection between the replacement eyedropper tip (401) and application tool (407) may serve as a barrier from the surrounding environment, serving a similar function as the eyedropper bottle's (101) original cap. Alternatively, each of the replacement eyedropper tip (401) and application tool (407) may be separately sterilized and combined in a sterile environment.

As discussed above, the replacement eyedropper tip (401) may include a collar (403) that allows the replacement eyedropper tip (401) to be directly threaded onto the set of threads (107) that are typically used to secure a cap (109) on the eyedropper bottle (101). This threading of the replacement eyedropper tip (401) onto the threads (107) may secure the replacement eyedropper tip (401) to the eyedropper bottle (101). Accordingly, the collar (403) will have corresponding threads on its interior that correspond to the threads (107) on the eyedropper bottle (101). Once the replacement eyedropper tip (401) has been fully threaded onto the eyedropper bottle (401), the application tool (401) may be removed for use. Typically, the application tool (401) will then serve as a protective snap on/off cap, The application tool (407) may first be used to apply the replacement eyedropper tip (401) to the eyedropper bottle (101), as discussed above. The application tool (407) may then be used to cover the installed replacement eyedropper tip (401) when the eyedropper bottle (101) is not in use. This use of the application tool (407) as a cap may then shield the replacement eyedropper tip (401) from contamination during periods of non-use. Further, because the application tool (407) may rely upon a friction fit between the application tool (407) and the replacement eyedropper tip (401), there is no need for the application tool (407) to have any threading. Accordingly, in this embodiment, the application tool (407) may be made to be lighter and less expensive than some of the other embodiments at least because the application tool (407) is easier to manufacture. In some embodiments, each component of the system may be made of the same material, such as, without limitation, high-density polyethylene (HDPE) or another polymer.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

It will further be understood that any of the ranges, values, properties, or characteristics given for any single component of the present disclosure can be used interchangeably with any ranges, values, properties, or characteristics given for any of the other components of the disclosure, where compatible, to form an embodiment having defined values for each of the components, as given herein throughout. Further, ranges provided for a genus or a category can also be applied to species within the genus or members of the category unless otherwise noted.

Finally, the qualifier "generally," and similar qualifiers as used in the present case, would be understood by one of ordinary skill in the art to accommodate recognizable attempts to conform a device to the qualified term, which may nevertheless fall short of doing so. This is because terms such as "circular" are purely geometric constructs and no real-world component is a true "circular" in the geometric sense. Variations from geometric and mathematical descriptions are unavoidable due to, among other things, manufacturing tolerances resulting in shape variations, defects and imperfections, non-uniform thermal expansion, and natural wear. Moreover, there exists for every object a level of magnification at which geometric and mathematical descriptors fail due to the nature of matter. One of ordinary skill would thus understand the term "generally" and relationships contemplated herein regardless of the inclusion of such qualifiers to include a range of variations from the literal geometric meaning of the term in view of these and other considerations.

The invention claimed is:

1. A method for replacing an existing eyedropper tip with a replacement eyedropper tip, the method comprising:

providing an eyedropper bottle having:

- the existing eyedropper tip, said existing eyedropper tip including:
  - a top region comprising a nose; and
  - a lower region having an outer surface;
- an upper region including:
  - an inner surface; and
  - exterior threads for supporting an existing cap;

wherein said outer surface of said existing eyedropper tip engages said inner surface of said upper region via an interference fit;

attaching a replacement tool to said nose of said existing eyedropper tip;

using said replacement tool to break said interference fit and separate said existing eyedropper tip from said eyedropper bottle while maintaining said attachment of said replacement tool to said existing eyedropper tip;

screwing said replacement eyedropper tip onto said exterior threads, said replacement eyedropper tip formed with internal threads positioned in a hollowed out space below a replacement eyedropper nose;

having a repeatedly separable top region of said replacement tip enclosing said replacement eyedropper nose, said repeatedly separable top region separating from said replacement eyedropper nose when said eyedropper is in use and while said internal threads remain engaged with said exterior threads.

2. The method of claim 1, further comprising:

removing a film enclosing said replacement tip prior to screwing said internal threads onto said external threads.

3. The method of claim 1 wherein said replacement tool engages said nose with grabber threads.

4. The method of claim 3 wherein said grabber threads have a threading diameter which is not constant.

5. The method of claim 1 wherein said replacement eyedropper nose produces a drop a different size from a drop produced by said existing eyedropper tip.

6. The method of claim 1 wherein said replacement eyedropper nose produces drops having a volume of less than 45 microliters.

7. The method of claim 1 wherein said replacement eyedropper nose produces a drop having a different shape from a drop produced by said existing eyedropper tip.

8. A method for replacing an existing eyedropper tip with a replacement eyedropper tip, the method comprising:

providing an eyedropper bottle having:

the existing eyedropper tip, said existing eyedropper tip including:

a top region comprising a nose; and a lower region having an outer surface;

an upper region including:

an inner surface; and exterior threads for supporting an existing cap;

wherein said outer surface of said existing eyedropper tip engages said inner surface of said upper region via an interference fit;

breaking said interference fit and separating said existing eyedropper tip from said eyedropper bottle;

screwing said replacement eyedropper tip onto said exterior threads, said replacement eyedropper tip formed with internal threads positioned in a hollowed out space below a replacement eyedropper nose;

having a repeatedly separable top region of said replacement tip enclosing said replacement eyedropper nose, said repeatedly separable top region separating from said replacement eyedropper nose when said eyedropper is in use and while said internal threads remain engaged with said exterior threads.

9. The method of claim 8, further comprising:

removing a film enclosing said replacement tip prior to screwing said internal threads onto said external threads.

10. The method of claim 8 wherein said breaking said interference fit comprises:

engaging a replacement tool with said nose using grabber threads in said replacement tool; and removing said existing eyedropper tip and said replacement tool together.

11. The method of claim 10 wherein said grabber threads have a threading diameter which is not constant.

12. The method of claim 8 wherein said replacement eyedropper nose produces a drop a different size from a drop produced by said existing eyedropper tip.

13. The method of claim 8 wherein said replacement eyedropper nose produces drops having a volume of less than 45 microliters.

14. The method of claim 8 wherein said replacement eyedropper nose produces a drop having a different shape from a drop produced by said existing eyedropper tip.

* * * * *